US010893804B2

United States Patent
Paschalis

(10) Patent No.: US 10,893,804 B2
(45) Date of Patent: Jan. 19, 2021

(54) MEASUREMENT OF INTRAOCULAR PRESSURE

(71) Applicant: Massachusetts Eye and Ear Infirmary, Boston, MA (US)

(72) Inventor: Eleftherios Ilios Paschalis, Quincy, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 348 days.

(21) Appl. No.: 15/765,023

(22) PCT Filed: Oct. 4, 2016

(86) PCT No.: PCT/US2016/055296
§ 371 (c)(1),
(2) Date: Mar. 30, 2018

(87) PCT Pub. No.: WO2017/062347
PCT Pub. Date: Apr. 13, 2017

(65) Prior Publication Data
US 2018/0279876 A1    Oct. 4, 2018

Related U.S. Application Data

(60) Provisional application No. 62/237,303, filed on Oct. 5, 2015.

(51) Int. Cl.
*A61B 3/16* (2006.01)
*A61F 2/14* (2006.01)
(Continued)

(52) U.S. Cl.
CPC .............. *A61B 3/16* (2013.01); *A61F 2/142* (2013.01); *A61F 2/16* (2013.01); *G01L 11/025* (2013.01);
(Continued)

(58) Field of Classification Search
CPC ... G01L 11/025; A61B 2562/228; A61B 3/16; A61B 2562/0247; A61B 2562/0266; A61F 2/16; A61F 2/142
See application file for complete search history.

(56) References Cited

U.S. PATENT DOCUMENTS 4,884,450 A * 12/1989 Greenwood ........... G01D 5/268
                                                                                 73/702
5,873,840 A     2/1999 Neff
(Continued)

OTHER PUBLICATIONS

International Search Report and Written Opinion in International Application No. PCT/US2016/055296, dated Dec. 15, 2016 13 pages.
(Continued)

*Primary Examiner* — Christine H Matthews
*Assistant Examiner* — Joshua Daryl D Lannu
(74) *Attorney, Agent, or Firm* — Fish & Richardson P.C.

(57) ABSTRACT

A system for measuring intraocular pressure in an eye of a patient includes a sensor configured to be positioned in the eye of the patient. The sensor includes a sealed cavity, and a flexible membrane sealing a distal end of the sealed cavity, the flexible membrane configured to deflect responsive to the intraocular pressure in the eye of the patient. The system includes a detection device configured to be positioned external to the eye of the patient and optically coupled to the sensor, the detection device configured to detect an indication of change in length of the sealed cavity resulting from deflection of the flexible membrane.

24 Claims, 5 Drawing Sheets

(51) Int. Cl.
*A61F 2/16* (2006.01)
*G01L 11/02* (2006.01)
(52) U.S. Cl.
CPC .............. *A61B 2562/0247* (2013.01); *A61B 2562/0266* (2013.01); *A61B 2562/228* (2013.01)

(56) References Cited

U.S. PATENT DOCUMENTS

| | | |
|---|---|---|
| 6,579,235 B1 | 6/2003 | Abita et al. |
| 2002/0052544 A1 | 5/2002 | Jeffries et al. |
| 2012/0041552 A1* | 2/2012 | Chuck ............... A61B 5/0084 623/6.11 |
| 2012/0116255 A1 | 5/2012 | Wang et al. |

OTHER PUBLICATIONS

International Preliminary Report on Patentability in International Application No. PCT/US2016/055296, dated Apr. 19, 2018, 8 pages.

* cited by examiner

MEASUREMENT OF INTRAOCULAR PRESSURE

CLAIM OF PRIORITY

This application is a 371 U.S. National Phase Application of PCT/US2016/055296, filed on Oct. 4, 2016, which claims priority to U.S. Patent Application Ser. No. 62/237,303, filed on Oct. 5, 2015, the entire contents of which are incorporated here by reference.

BACKGROUND

Increased intraocular pressure (IOP) is a significant factor contributing to glaucoma disease and progression, which can eventually lead to blindness. Patients with implanted artificial corneas are often at higher risk for glaucoma development or progression.

SUMMARY

We describe here an approach to measuring the intraocular pressure (IOP) within the eye of a patient. A sensor is positioned in the eye of the patient. The sensor includes a sealed cavity that acts as an optical resonator. A flexible membrane seals the distal end of the sealed cavity. The flexible membrane deflects responsive to the intraocular pressure in the eye of the patient, thus causing a change in the length of the sealed cavity and hence a change in the resonance frequency of light in the cavity. A detection device external to the eye of the patient is optically coupled to the sensor via a lens on the detection device and a lens on the sensor. The detection device interrogates the sensor with multiple wavelengths of light to identify the resonance frequency of the sealed cavity. Based on the resonance frequency, the length of the cavity can be determined, from which the intraocular pressure within the eye of the patient can be determined.

In an aspect, a system for measuring intraocular pressure in an eye of a patient includes a sensor configured to be positioned in the eye of the patient. The sensor includes a sealed cavity, and a flexible membrane sealing a distal end of the sealed cavity, the flexible membrane configured to deflect responsive to the intraocular pressure in the eye of the patient. The system includes a detection device configured to be positioned external to the eye of the patient and optically coupled to the sensor, the detection device configured to detect an indication of change in length of the sealed cavity resulting from deflection of the flexible membrane.

Embodiments can have one or more of the following features.

The sensor includes an optical fiber having a proximal end and a distal end, the sealed cavity disposed at the distal end and the proximal end configured to be optically coupled to the detection device.

The system includes one or more of a lens, a flat polished surface, and a flat angled surface at the proximal end of the optical fiber.

The detection device is configured to be optically coupled to the sensor without being in physical contact with the sensor.

The deflection of the flexible membrane is proportional to the intraocular pressure.

The flexible membrane is formed of a reflective material.

A proximal end of the sealed cavity is sealed with a semitransparent, reflective material.

The sensor is configured to be integrated into a prosthetic cornea or intraocular lens (IOL).

The sensor is configured to be secured into the prosthetic cornea or lens using a polymer sealant.

The change in length of the sealed cavity causes a change in a resonance frequency of light in the sealed cavity.

The detection device is configured to detect a resonance frequency of light in the sealed cavity, and wherein the resonance frequency of light depends on the length of the sealed cavity.

The detection device is configured to be optically coupled to the sensor without being in physical contact with the sensor.

The detection device includes a light source configured to produce light for illumination of the sensor; and a detector configured to detect a frequency of light received from the sensor.

The frequency of light received from the sensor corresponds to a resonance frequency of the sealed cavity.

The detection device includes an optical fiber having a proximal end and a distal end, the distal end of the optical fiber configured to be optically coupled to the sensor.

The system includes a lens at the distal end of the optical fiber.

In an aspect, a device for measuring intraocular pressure in an eye of a patient includes an optical fiber having a proximal end and a distal end, the proximal end of the optical fiber configured to be optically coupled to a detection device external to the eye of the patient. The device includes a pressure sensor disposed at a distal end of the optical fiber, the pressure sensor includes a sealed cavity, and a flexible membrane sealing a distal end of the sealed cavity, the flexible membrane configured to deflect responsive to the intraocular pressure in the eye of the patient. Deflection of the flexible membrane causes a change in a length of the sealed cavity.

Embodiments can include one or more of the following features.

The change in length of the sealed cavity causes a change in a resonance frequency of light in the sealed cavity.

The device includes a lens disposed at the distal end of the optical fiber.

The deflection of the flexible membrane is proportional to the intraocular pressure.

The flexible membrane is formed of a reflective material.

A proximal end of the sealed cavity is sealed with a semitransparent, reflective material.

The device is configured to be integrated into a prosthetic cornea or lens.

In an aspect, a method for measuring intraocular pressure in an eye of a patient includes optically coupling a detection device to a sensor positioned in the eye of the patient. The sensor includes a sealed cavity, and a flexible membrane sealing a distal end of the sealed cavity, the flexible membrane configured to deflect responsive to the intraocular pressure in the eye of the patient. Deflection of the flexible membrane causes a change in length of the sealed cavity. The method includes detecting a resonance frequency of light in the sealed cavity, the frequency of light depending on the length of the sealed cavity; and determining the intraocular pressure in the eye of the patient based on the resonance frequency of light in the sealed cavity.

Embodiments can include one or more of the following features.

Detecting the resonance frequency of light in the sealed cavity includes illuminating the sealed cavity with multiple wavelengths of light; and detecting the frequency of light received at the detection device from the sealed cavity.

Optically coupling the detection device to the sensor includes optically coupling the detection device to the sensor without physical contact between the detection device and the sensor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Implantation of artificial corneas, such as the Boston Keratoprosthesis (BKPro) artificial cornea, eliminates the ability to perform intraocular pressure (IOP) measurements using standard tonometers that rely on corneal applanation or indentation. When an artificial cornea is implanted in an eye, finger palpation on the sclera is performed to determine intraocular pressure, which often results in unreliable subjective measurements and presents the risk that high intraocular pressure is not detected. High intraocular pressure is the most significant factor contributing to glaucoma disease and progression, which eventually leads to blindness. Lowering the intraocular pressure of a patient, either with medication or surgically, can help protect against glaucoma. Patients with implanted artificial corneas are known to be at higher risk for development or progression of glaucoma. Providing an approach to reliable and accurate measurement of intraocular pressure in patients with artificial corneas can help improve long term visual outcomes and successful use of the artificial cornea.

We describe here the integration of an optical pressure sensor in the stem of an artificial cornea, such as the BKPro device, or another keratoprosthetic device, such as a prosthetic cornea or intraocular lens. The keratoprosthetic device can be made of transparent poly(methylmethacrylate) (PMMA) synthetic plastic or another transparent material.

Figure 1:
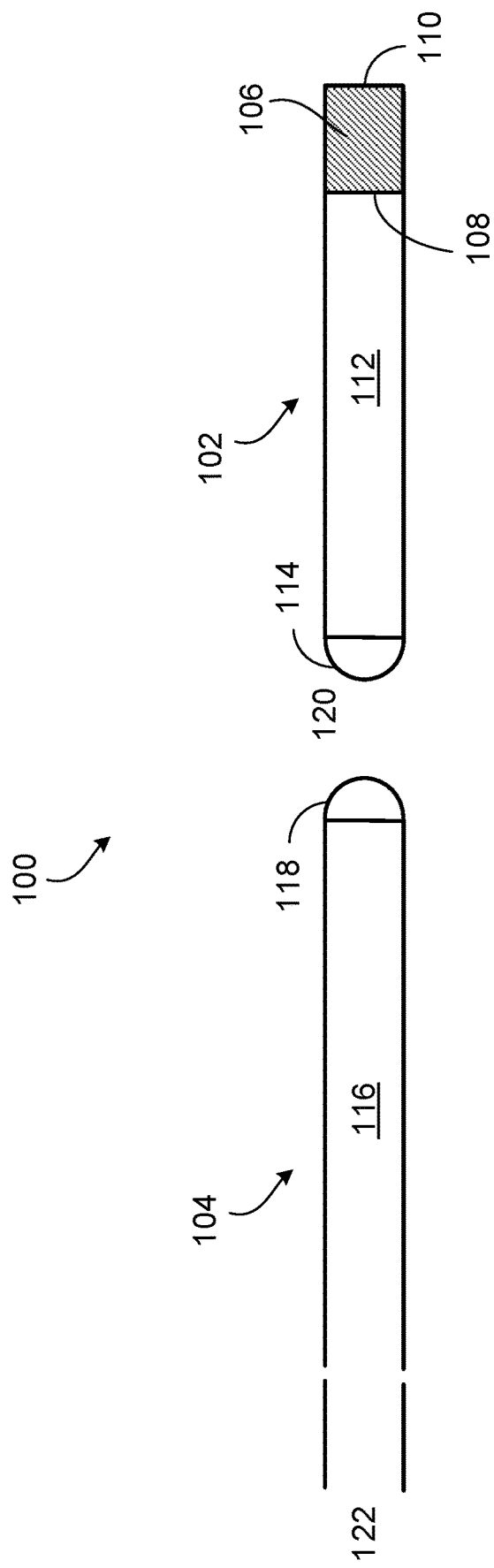
FIG. 1 is a diagram of a pressure sensor.
Figure 2A:
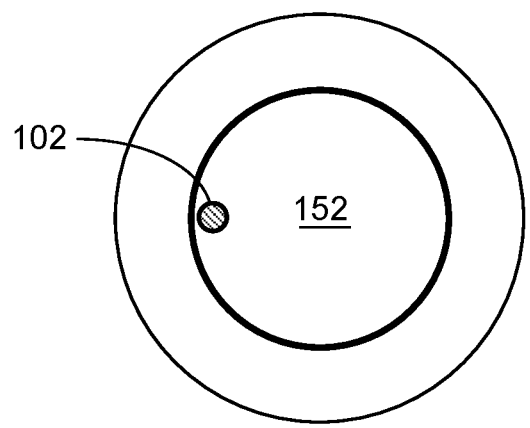
FIGS. 2A and 2B are a top view and a side view, respectively, of a pressure sensor integrated into an artificial cornea.
Figure 2B:
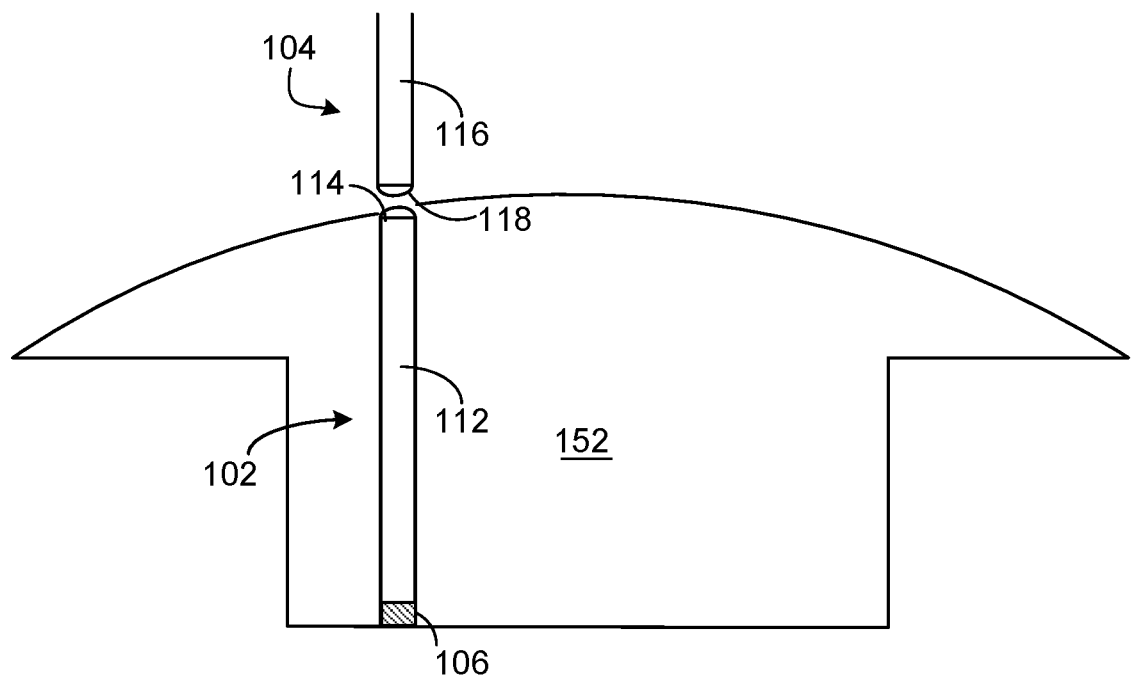
Figure 3:
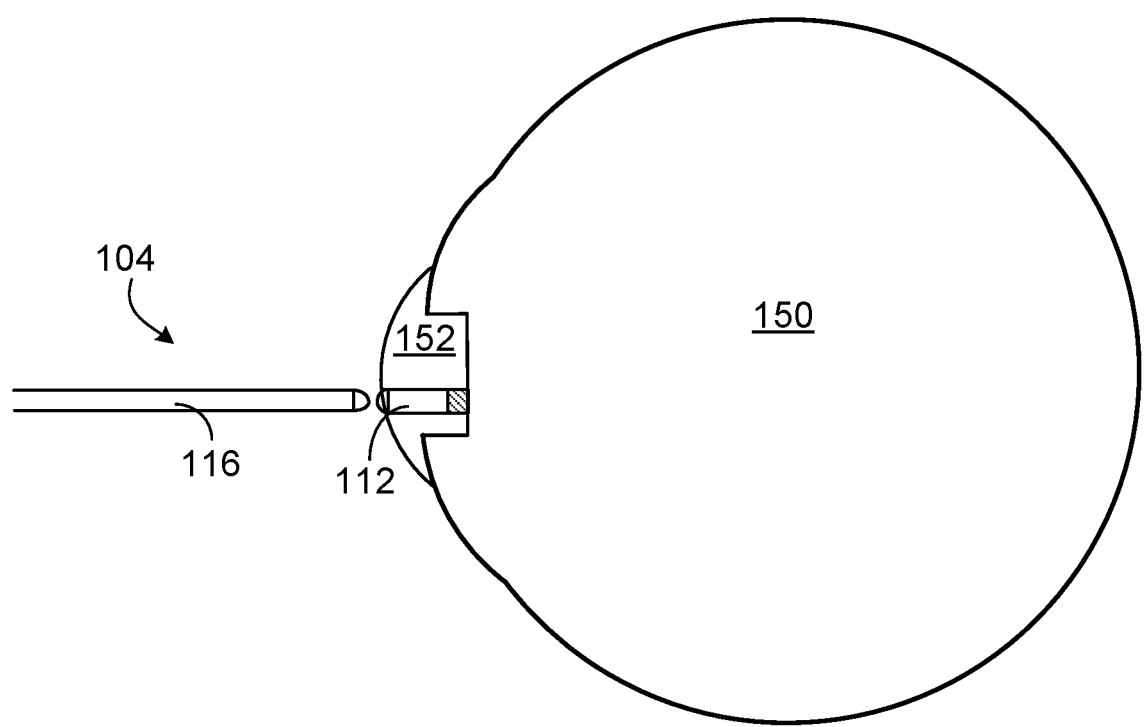
FIG. 3 is a diagram of a pressure sensor and artificial cornea implanted in an eye.

Referring to FIGS. 1-3, a device 100 for sensing of intraocular pressure in an eye 150 includes an internal segment 102 that can be integrated into the stem of an artificial cornea 152, such as a BKPro artificial cornea, and an external segment 104 that is optically coupled to the internal segment 102. The internal segment 102 includes an optical pressure sensor, such as a Fabry-Perot optical cavity 106 (referred to here as an optical cavity 102), that is sensitive to changes in intraocular pressure in the eye 150. In particular, a resonance frequency of the optical cavity 106 changes in response to changes in intraocular pressure. The resonance frequency of the optical cavity 106 can be detected by a detector coupled to the external segment 104, from which the intraocular pressure in the eye 150 can be determined.

The optical cavity 102 is bounded on its distal end by a fixed surface 108 that acts as a semitransparent reflector, and on its proximal end by a deformable surface 110 that acts as a substantially 100% reflector. For instance, the deformable surface 110 can be formed of a reflective, flexible membrane that hermetically seals the optical cavity 106.

When the internal segment 102 of the device 100 is integrated into the artificial cornea 152 implanted in the eye 150, the deformable surface 110 is in contact with the aqueous humor in the anterior chamber of the eye 150. Intraocular pressure causes the aqueous humor within the eye 150 to exert a pressure on the deformable surface 110, deflecting the deformable surface 110 inwards towards the interior of the optical cavity 106. The degree of deformation of the deformable surface 110 is proportional to the intraocular pressure (within a specified range, such as a range of expected intraocular pressures). Deformation of the deformable surface 110 causes a change in the distance between the deformable surface 110 and the fixed surface 108, thus changing the length of the optical cavity 106 and causing a shift in the resonance frequency of light within the optical cavity 106. The resonance frequency of light within the optical cavity 106 is thus an indication of the intraocular pressure.

To interrogate the resonance frequency of light within the optical cavity 106, the optical cavity 106 is externally illuminated with multiple wavelengths of light and the wavelength that causes resonance within the optical cavity 106 is determined. Light can be transferred from an external light source (not shown) to the optical cavity 106 by a short fiber optic waveguide 112 optically coupled to the optical cavity 106. The fiber optic waveguide 112 can be integrated into the stem of the artificial cornea. The distal end 114 of the fiber optic waveguide 112 can have a polished end that that terminates on the anterior surface of the stem of the artificial cornea (e.g., the curved lens of a BKPro artificial cornea). The polished distal end 114 can be a flat surface, an angled surface, a convex surface, a concave surface, or another type of surface that acts as a micro-lens. In some examples, aberration correction can be employed using aspheric lens design.

Interrogation of the intraocular pressure is performed by illuminating the fiber optic waveguide 112 by a light source (not shown) external to the eye. The light source can be a polychromatic light source or a frequency shifting monochromatic light source, such as a light emitting diode (LED), a laser, or another type of light source. Light from the light source can be delivered to the fiber optic waveguide 112 via a long external fiber optic 116 that is positioned external to the eye. The external fiber optic 116 can have a polished proximal end 118, such as a flat surface, an angled surface, a convex surface, a concave surface, or another type of surface that acts as a micro-lens. In some examples, aberration correction can be employed using aspheric lens design. The external fiber optic 116 can be positioned substantially vertically, external to the eye, and with the polished proximal end 118 in close proximity to the polished distal end 114 of the fiber optic waveguide 112. The polished proximal end 118 of the external fiber optic 116 is coupled via a non-contact coupling to the polished distal end 114 of the fiber optic waveguide 112 such that the light can be focused from the external fiber optic 116 into the fiber optic waveguide 112. In some examples, an interface medium 120 can be provided to facilitate coupling between the polished proximal end 118 of the external fiber optic 116 and the polished distal end 114 of the fiber optic waveguide, such as air, water, hydrogel, or another medium.

To interrogate the resonance frequency of the optical cavity 106, the light is focused into the fiber optic waveguide 112 from the external fiber optic 116 and transmitted along the fiber optic waveguide 112 to the optical cavity 106. When the optical cavity 106 is illuminated with light at its resonance frequency, significant energy is reached within the cavity, causing a fraction of the resonated light to escape through the fixed, semi-reflective surface 108 of the optical cavity 102. The escaped light is transmitted along the fiber optic waveguide 112 within the eye, into the external fiber optic 116, and to a wavelength or frequency detector 122. The wavelength or frequency detector 122, such as a broad band frequency detector, e.g., an optical wavelength or frequency analyzer, is connected to the light source and optically coupled to the polished distal end 114 of the fiber optic waveguide 112.

The wavelength or frequency of the escaped light can then be correlated to the length of the optical cavity 106 and from there to intraocular pressure, e.g., through software and a nomogram.

In some examples, the optical cavity 106 can operate within the optical spectrum (e.g., having a resonance wavelength of between about 400 nm and about 700 nm), to minimize the footprint and maximize the sensitivity of the optical cavity 106.

In the device 100, a fiber optic waveguide 112 and an optical cavity 106 are integrated into the stem of an artificial cornea to form an integrated pressure system. In some examples, to avoid disturbances in vision, the fiber optic waveguide 112 and the optical cavity 102 can be placed at a peripheral section of the stem of the artificial cornea. For instance, a narrow tunnel (e.g., a tunnel with a diameter of about 200 μm, about 200 μm, about 200 μm, about 200 μm, or another diameter, can be formed in the peripheral optical section of the artificial cornea 152 and the internal segment 102 of the device 100 can be inserted into the tunnel. In some examples, the polishing of the distal end 114 of the fiber optic waveguide 112 can also help to avoid disturbances in vision. In some examples, more than one internal segment 102 can be integrated into the stem of a single artificial cornea to increase reliability and accuracy in measurements.

In some examples, an alignment device can be used to align the polished distal end 114 of the fiber optic waveguide 112 integrated into the artificial cornea 152 with the polished proximal end 118 of the external fiber optic 116. For instance, the alignment device can be a holder that holds the patient, the external fiber optic 116, or both, in a stationary position. In some examples, the alignment can be performed under a microscope, under a slit lamp, or in another environment that facilitates alignment of small components.

The use of the fiber optic waveguide 112 and the optical cavity 106 integrated into the stem of an artificial cornea can eliminate the need for implantation of a pressure sensor directly within the eye, such as occurs, e.g., with implantable interocular lenses with wireless pressure transducers for measuring intraocular pressure. The device 100 provides a complete, robust solution for measuring intraocular pressure in artificial cornea patients. In some examples, the fiber optic waveguide 112 and the optical cavity 106 of the device 100 can be integrated into other kinds of keratoprosthesis devices. In some examples, the device 100 can be used to perform intraocular pressure measurements away from a medical facility, e.g., at home. The data can be transmitted to a doctor through a wireless communication technology, such as wireless Internet, Bluetooth, a cellular network, or another wireless communication technology.

Figure 4:
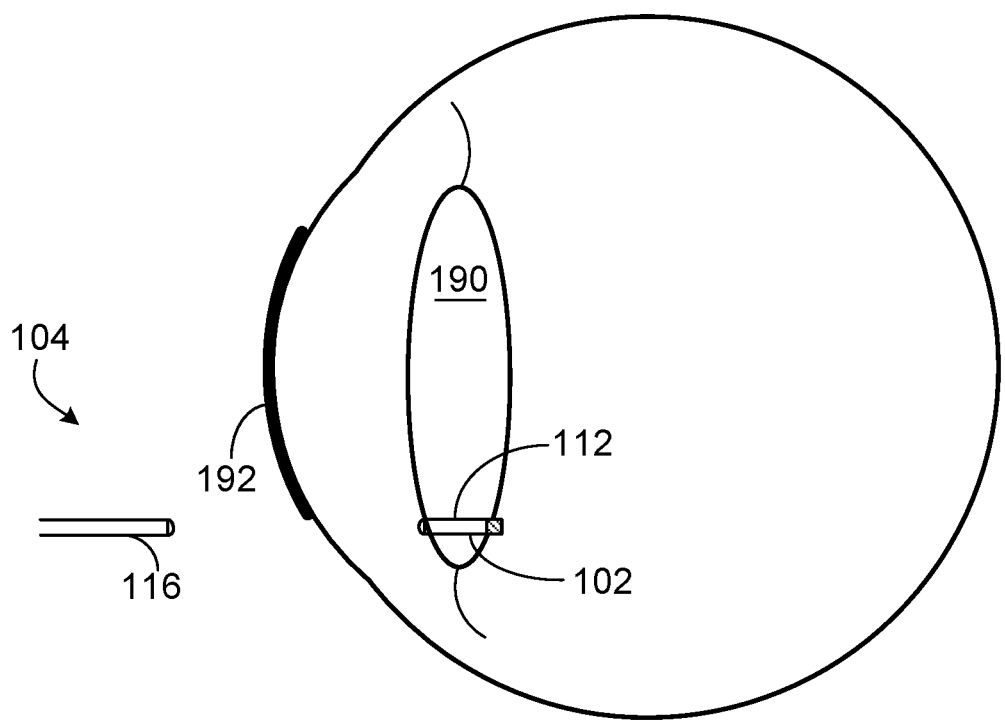
FIG. 4 is a diagram of a pressure sensor integrated into an artificial lens implanted in an eye.

Referring to FIG. 4, in some examples, the internal segment 102 including the fiber optic waveguide 112 and the optical cavity 106 can be integrated into an intraocular lens 190. The intraocular lens 190 can be implanted in either the anterior or the posterior chamber of the eye 150. Additional optical components, such as external lenses, can be used to couple the external fiber optic 116 to the fiber optic waveguide 112 across the cornea 192 of the eye 150 when the device is used in an intraocular lens 190.

Figure 5A:
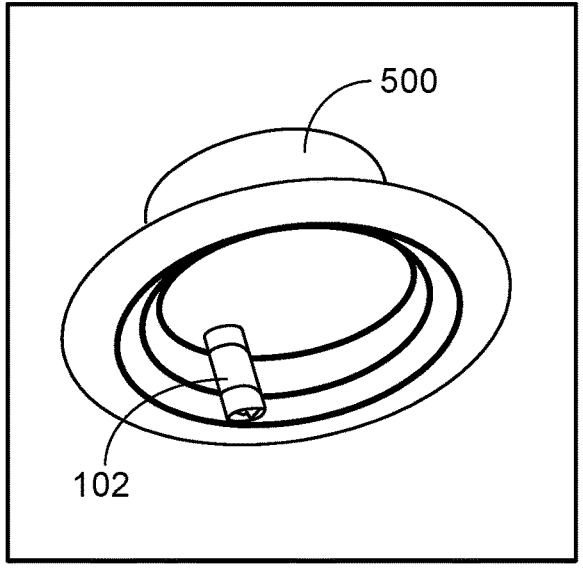
FIGS. 5A, 5B, and 5C are diagrams of a pressure sensor.
Figure 5B:
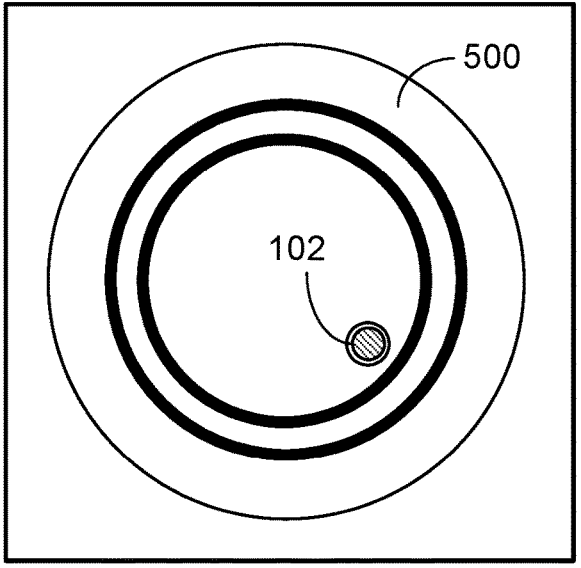
Figure 5C:
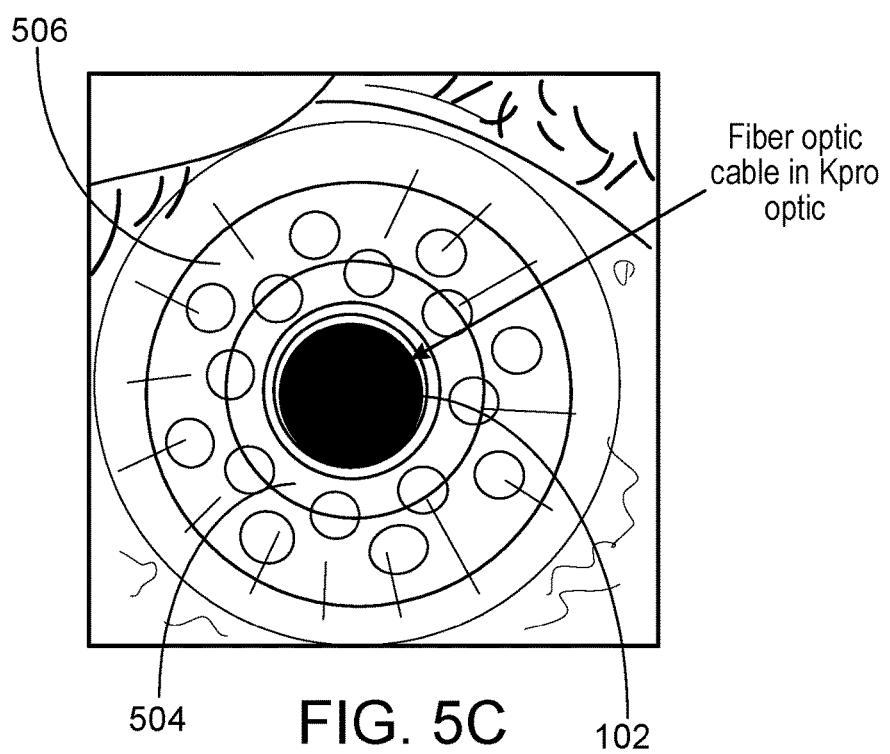

Referring to FIGS. 5A-5C, a stem 500 of a BKpro artificial cornea is shown with a tunnel on the periphery of the stem 500. The internal segment 102 of a device for sensing intraocular pressure is inserted into the tunnel in the stem 500 of the artificial cornea. The device has a diameter of about 300 μm. FIGS. 5A and 5B show a side view and top view, respectively, of the stem 500. FIG. 5C is a photograph of an artificial cornea 504 implanted in a human eye 506, with the internal segment 102 of the device 100 inserted therein.

The approaches described here for integrating optical pressure sensors into artificial corneas or other keratoprosthetic devices means that no additional surgery is performed for implantation of a distinct optical pressure sensing device. The avoidance of additional surgery can help reduce the risk of anterior chamber congestion, angle closure, pressure glaucoma, or other effects. The device described here can be inserted into and removed from the artificial cornea without surgery, thus making use of this device easy and relatively non-invasive and making replacement of the device, e.g., in the event of device failure, a straightforward procedure. For instance, the internal segment 102 of the device can be secured in the artificial cornea, e.g., an artificial cornea formed of poly(methylmethacrylate) (PMMA), using a polymer sealant such as a siloxane or polydimethylsiloxance (PDMS) that allows for removal or repositioning of the device.

Other implementations are also within the scope of the following claims.

What is claimed is:

1. A system for measuring intraocular pressure in an eye of a patient, the system comprising:
 a sensor configured to be positioned in the eye of the patient, the sensor comprising:
  a sealed cavity, and
  a flexible membrane sealing a distal end of the sealed cavity, the flexible membrane configured to deflect responsive to the intraocular pressure in the eye of the patient; and
 a detection device configured to be positioned external to the eye of the patient, the detection device configured to detect an indication of change in length of the sealed cavity resulting from deflection of the flexible membrane,
  the detection device comprising an optical fiber having a proximal end and a distal end, the distal end of the optical fiber configured to be optically coupled to the sensor.

2. The system of claim 1, wherein the sensor comprises a second optical fiber having a proximal end and a distal end, the sealed cavity disposed at the distal end and the proximal end configured to be optically coupled to the detection device.

3. The system of claim 2, comprising one or more of a lens, a flat polished surface, and a flat angled surface at the proximal end of the second optical fiber.

4. The system of claim 2, wherein the detection device is configured to be optically coupled to the sensor without being in physical contact with the sensor.

5. The system of claim 1, wherein the deflection of the flexible membrane is proportional to the intraocular pressure.

6. The system of claim 1, wherein the flexible membrane is formed of a reflective material.

7. The system of claim 1, wherein a proximal end of the sealed cavity is sealed with a semitransparent, reflective material.

8. The system of claim 1, wherein the sensor is configured to be integrated into a prosthetic cornea or intraocular lens (IOL).

9. The system of claim 8, wherein the sensor is configured to be secured into the prosthetic cornea or lens using a polymer sealant.

10. The system of claim 1, wherein the change in length of the sealed cavity causes a change in a resonance frequency of light in the sealed cavity.

11. The system of claim 1, wherein the detection device is configured to detect a resonance frequency of light in the sealed cavity, and wherein the resonance frequency of light depends on the length of the sealed cavity.

12. The system of claim 1, wherein the detection device is configured to be optically coupled to the sensor without being in physical contact with the sensor.

13. The system of claim 1, wherein the detection device comprises:
a light source configured to produce light for illumination of the sensor; and
a detector configured to detect a frequency of light received from the sensor.

14. The system of claim 13, wherein the frequency of light received from the sensor corresponds to a resonance frequency of the sealed cavity.

15. The system of claim 1, comprising a lens at the distal end of the optical fiber.

16. A device for measuring intraocular pressure in an eye of a patient, the device comprising:
an optical fiber having a proximal end and a distal end, the proximal end of the optical fiber configured to be optically coupled to a detection device external to the eye of the patient;
a pressure sensor disposed at a distal end of the optical fiber, the pressure sensor comprising:
a sealed cavity, wherein a proximal end of the sealed cavity is sealed with a semitransparent, reflective material, and
a flexible membrane sealing a distal end of the sealed cavity, the flexible membrane configured to deflect responsive to the intraocular pressure in the eye of the patient,
wherein deflection of the flexible membrane causes a change in a length of the sealed cavity.

17. The device of claim 16, wherein the change in length of the sealed cavity causes a change in a resonance frequency of light in the sealed cavity.

18. The device of claim 16, comprising a lens disposed at the distal end of the optical fiber.

19. The device of claim 16, wherein the deflection of the flexible membrane is proportional to the intraocular pressure.

20. The device of claim 16, wherein the flexible membrane is formed of a reflective material.

21. The device of claim 16, wherein the device is configured to be integrated into a prosthetic cornea or lens.

22. A method for measuring intraocular pressure in an eye of a patient, the method comprising:
optically coupling a detection device to a sensor positioned in the eye of the patient, the sensor comprising:
a sealed cavity, and
a flexible membrane sealing a distal end of the sealed cavity, the flexible membrane configured to deflect responsive to the intraocular pressure in the eye of the patient, wherein deflection of the flexible membrane causes a change in length of the sealed cavity, and
the detection device comprising an optical fiber having a proximal end and a distal end, the distal end of the optical fiber configured to be optically coupled to the sensor;
detecting a resonance frequency of light in the sealed cavity, the frequency of light depending on the length of the sealed cavity; and
determining the intraocular pressure in the eye of the patient based on the resonance frequency of light in the sealed cavity.

23. The method of claim 22, wherein detecting the resonance frequency of light in the sealed cavity comprises:
illuminating the sealed cavity with multiple wavelengths of light; and
detecting the frequency of light received at the detection device from the sealed cavity.

24. The method of claim 22, wherein optically coupling the detection device to the sensor comprises optically coupling the detection device to the sensor without physical contact between the detection device and the sensor.

* * * * *